United States Patent [19]

Ogden

[11] Patent Number: 5,682,878
[45] Date of Patent: Nov. 4, 1997

[54] START-UP RAMP SYSTEM FOR CPAP SYSTEM WITH MULTIPLE RAMP SHAPE SELECTION

[75] Inventor: Douglas R. Ogden, Arvada, Colo.

[73] Assignee: Respironics, Inc., Pittsburgh, Pa.

[21] Appl. No.: 569,829

[22] Filed: Dec. 7, 1995

[51] Int. Cl.⁶ .......................... A61M 16/00; A62B 7/00; F16K 31/02
[52] U.S. Cl. .................. 128/204.23; 128/204.18; 128/205.23
[58] Field of Search .................. 128/202.22, 204.18, 128/204.21–204.23, 204.26, 205.23

[56] References Cited

U.S. PATENT DOCUMENTS

| | | | |
|---|---|---|---|
| 5,117,819 | 6/1992 | Servidio et al. | 128/204.18 |
| 5,134,995 | 8/1992 | Gruenke et al. | 128/204.23 |
| 5,148,802 | 9/1992 | Sanders et al. | 128/204.18 |
| 5,188,098 | 2/1993 | Hoffman et al. | 128/204.23 |
| 5,199,424 | 4/1993 | Sullivan et al. | 128/204.18 |
| 5,211,170 | 5/1993 | Press | 128/204.18 |
| 5,239,995 | 8/1993 | Estes et al. | 128/204.23 |
| 5,313,937 | 5/1994 | Zdrojkowski | 128/202.22 |
| 5,335,654 | 8/1994 | Rapoport | 128/204.23 |
| 5,388,575 | 2/1995 | Taube | 128/204.23 |
| 5,398,676 | 3/1995 | Press et al. | 128/204.23 |
| 5,433,193 | 7/1995 | Sanders et al. | 128/204.18 |

*Primary Examiner*—Kimberly L. Asher
*Attorney, Agent, or Firm*—W. Scott Carson

[57] ABSTRACT

A start-up ramp system for CPAP and bilevel CPAP devices. The system offers the patient a choice of at least two, time-pressure ramp paths over a predetermined, fixed, initial time interval to a predetermined, fixed, initial therapeutic pressure. Both the initial time period and initial therapeutic pressure are set by the care giver and are non-adjustable by the patient. In operation, the patient then selects the ramp path of his or her choice to the pre-set pressure over the pre-set time period by depressing an actuator button which has a graphic or pictorial representation of the ramp path on it. Regardless of the ramp path selected, the CPAP device will reach the predetermined therapeutic pressure only after the predetermined time interval set by the care giver has lapsed.

20 Claims, 5 Drawing Sheets

START-UP RAMP SYSTEM FOR CPAP SYSTEM WITH MULTIPLE RAMP SHAPE SELECTION

BACKGROUND OF THE INVENTION

1. Field of the Invention

This invention relates to the field of initial or start-up ramps for continuous positive airway pressure (CPAP) devices and bilevel CPAP devices.

2. Discussion of the Background

The use of continuous positive airway pressure (CPAP) devices and bilevel CPAP devices has become widely accepted for the treatment of sleep apnea. Sleep apnea is believed to afflict up to about 3% of the general population and is characterized by a narrowing or closing of the upper airway passage that results in complete or nearly complete stoppage of respiration during sleep. The causes of sleep apnea vary from patient to patient but the most common ones are believed to be obesity, poor tone in the muscles lining the upper airway and in the muscles controlling the tongue, and excessive length and size of the soft palate in the back of the patient's throat. Regardless of the cause, the resulting restriction or closure of the airway passage during sleep and subsequent recurring, prolonged episodes of apnea (i.e., cessation of breathing) can lead to simple daytime sleepiness and listlessness to more severe and debilitating physical and mental condition, including congestive heart failure.

Drug therapy and surgical techniques such as tracheotomies have been used to treat sleep apnea. However, the use of CPAP and bilevel CPAP devices has become more popular as a preferred, non-invasive technique to treat the problem without the intervention of surgery or possible side effects of drug therapy. In this regard, CPAP devices as the name suggests simply apply a relatively small, continuous positive pressure (e.g., ten centimeters of water above atmospheric pressure) to the patient's airway to keep it in a continuously open state during sleep. Bilevel CPAP devices are somewhat more involved but still provide positive pressure at all times to keep the patient's airway continuously open. The applied positive pressure is however varied wherein it is greater during inhalation and then reduced during exhalation (i.e., bilevel).

A common problem encountered by patients using either CPAP or bilevel CPAP devices is that they find it difficult to initially fall asleep. In reality, even the relatively small therapeutic pressure (e.g., ten centimeters of water above atmospheric pressure) can be distracting to a patient trying to fall asleep. In this light, techniques were developed to gradually increase or ramp-up the applied pressure for the first thirty minutes or so of use allowing the patient to fall asleep. Consequently, instead of being initially confronted with the full therapeutic pressure, the patient was exposed to a very gradual increase or ramp-up to the full therapeutic pressure and was able to more easily fall asleep.

As such ramps became more popular, the CPAP devices were provided with more and more adjustability for the ramp variables of time and pressure and the patient in many cases was encouraged to adjust the variables (particularly time) to his or her own preference. The belief was that the patient would feel more in control of his or her therapy and more likely to use the devices. Since the devices are most commonly used by the patient in his or her home, patient compliance is indeed a critical consideration in prescribing CPAP and bilevel CPAP therapy. However, since most patients are not qualified nor trained to set the ramp-up pressures and times, the present inventor felt complete adjustability of these variables was actually undesirable yet he was sympathetic to the patient's desire to have some control over his or her therapy. Consequently, he developed a start-up ramp system for CPAP and bilevel CPAP devices which he believes satisfies both the desire of the doctor/care giver for precision in setting the therapeutic pressure and time variables as well as the desire of the patient for some control. More specifically, his invention allows the doctor/care giver to have a ramp-up feature fixed in time and therapeutic pressure (with neither variable being adjustable by the patient). At the same time, the invention offers the patient a choice of ramp-up paths to reach these predetermined, fixed time/pressure settings thereby satisfying the patient's desire for some control over his or her therapy.

SUMMARY OF THE INVENTION

This invention relates to a start-up ramp system for CPAP and bilevel CPAP devices. The system offers the patient a choice of at least two, time-pressure ramp paths over a predetermined, fixed, initial time interval to a predetermined, fixed, initial therapeutic pressure. Both the initial time period and initial therapeutic pressure are set by the care giver and are non-adjustable by the patient. In operation, the patient then selects the ramp path of his or her choice to the pre-set pressure over the pre-set time period by depressing an actuator button which has a graphic or pictorial representation of the ramp path on it. In the preferred embodiment, there are three ramp choices with one being linear and the other two being accelerating and decelerating curves. Regardless of the ramp path selected, the CPAP device will reach the predetermined therapeutic pressure only after the predetermined time interval set by the care giver has lapsed.

DETAILED DESCRIPTION OF THE PREFERRED EMBODIMENTS

Figure 1:
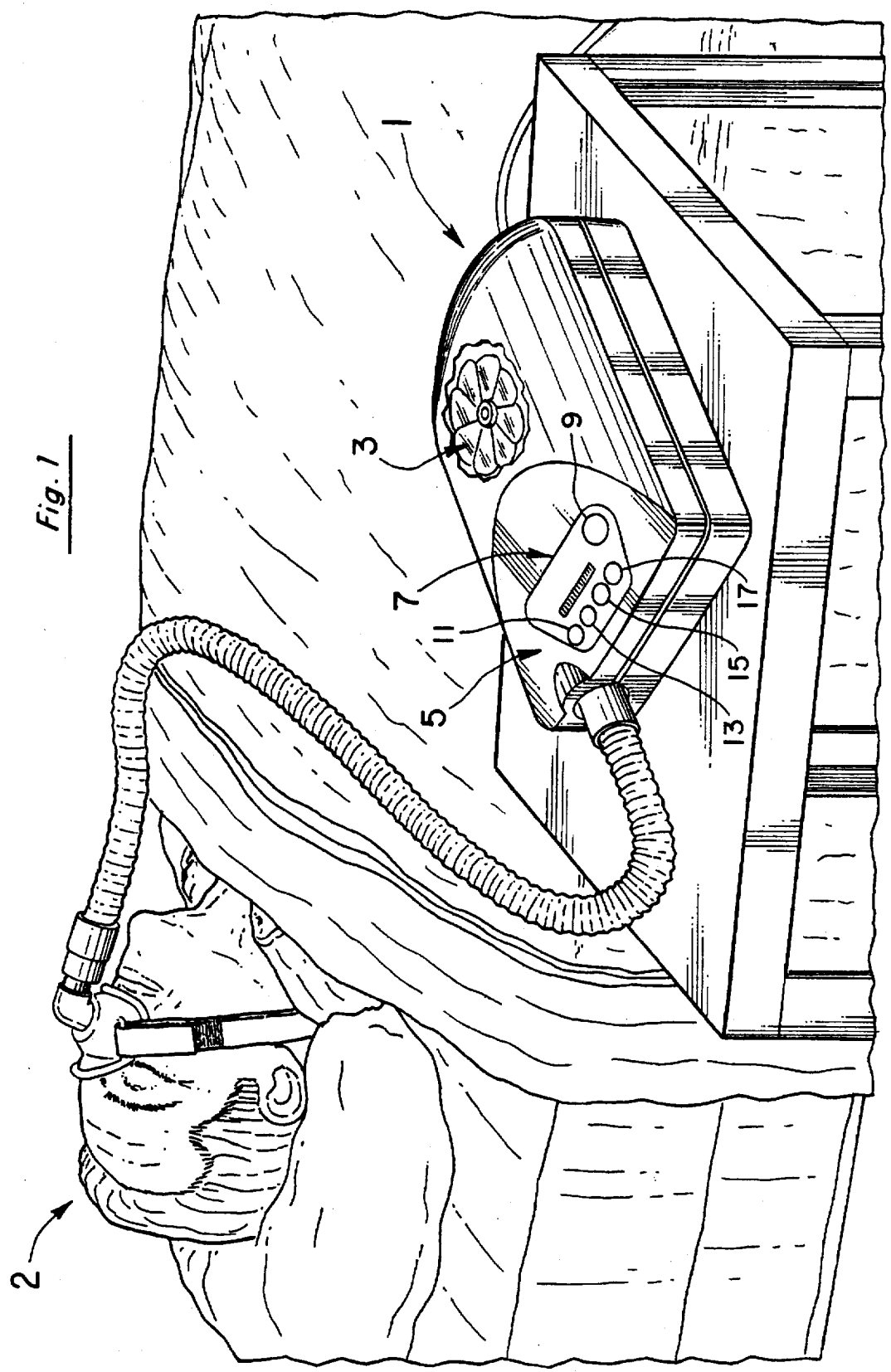
FIG. 1 is a perspective view of the CPAP respiratory device of the present invention shown in use with a patient.

The present invention as shown in FIG. 1 is primarily intended for use with a CPAP respiratory device 1 to aid a patient 2 suffering from sleep apnea. The CPAP (continuous positive airway pressure) device 1 can be either a monolevel or bilevel one. In either case, the device 1 serves to supply some increment of positive pressure at all times to the patient's upper airway to keep the airway from constricting or closing and initiating an attack of apnea (i.e., cessation of breathing).

The CPAP device 1 includes a variable speed blower or fan 3 which can deliver variable levels of pressurized air to the patient 2. In the preferred embodiment, the delivered pressure can be varied from about two centimeters of water to about 20 centimeters of water above atmospheric. In the initial or start-up operation of the respiratory device 1, a ramp feature is preferably included wherein an initial therapeutic or prescribed pressure (e.g., ten centimeters of water) set by the doctor, clinician, or other care giver is reached over an initial time interval (e.g., thirty minutes) which is also set by the doctor, clinician, or care giver. The initial therapeutic pressure in virtually all cases is determined according to a prescription issued by the doctor based on studies of the individual patient's condition. Similarly, the initial time interval is also determined according to the doctor's prescription. In both cases in the preferred embodiments, the predetermined, initial therapeutic pressure and predetermined, initial time interval of the doctor's prescription for the ramp are fixed by a care giver other than the patient 2 and are non-adjustable by the patient 2.

Figure 3:
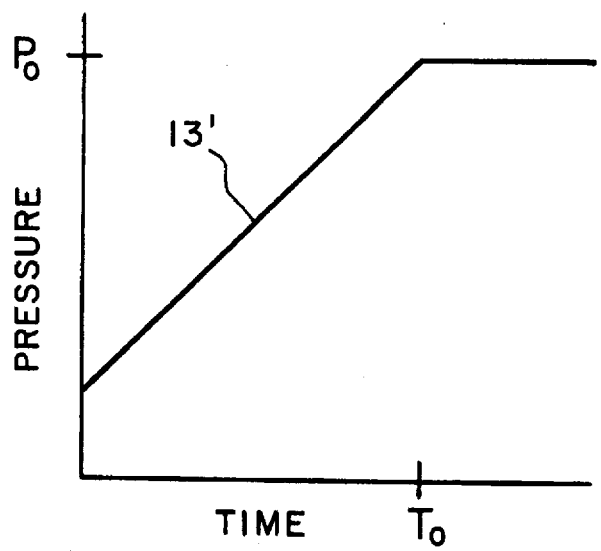
FIGS. 3-5 graphically illustrate the ramp-path choices offered by the present invention to the patient.

In this regard and even though the initial therapeutic pressure $P_o$ (see FIG. 3) and initial time interval $T_o$ (see also FIG. 3) are predetermined and fixed and non-adjustable by the patient 2, the patient 2 with the present invention is still given at least two and preferably three choices of the ramp-up path to reach these prescribed pressure $P_o$ and time $T_o$. The patient 2 is thus offered some choice and control over his or her CPAP therapy in an effort to increase the patient's comfort and compliance or use of the device 1.

Figure 2:
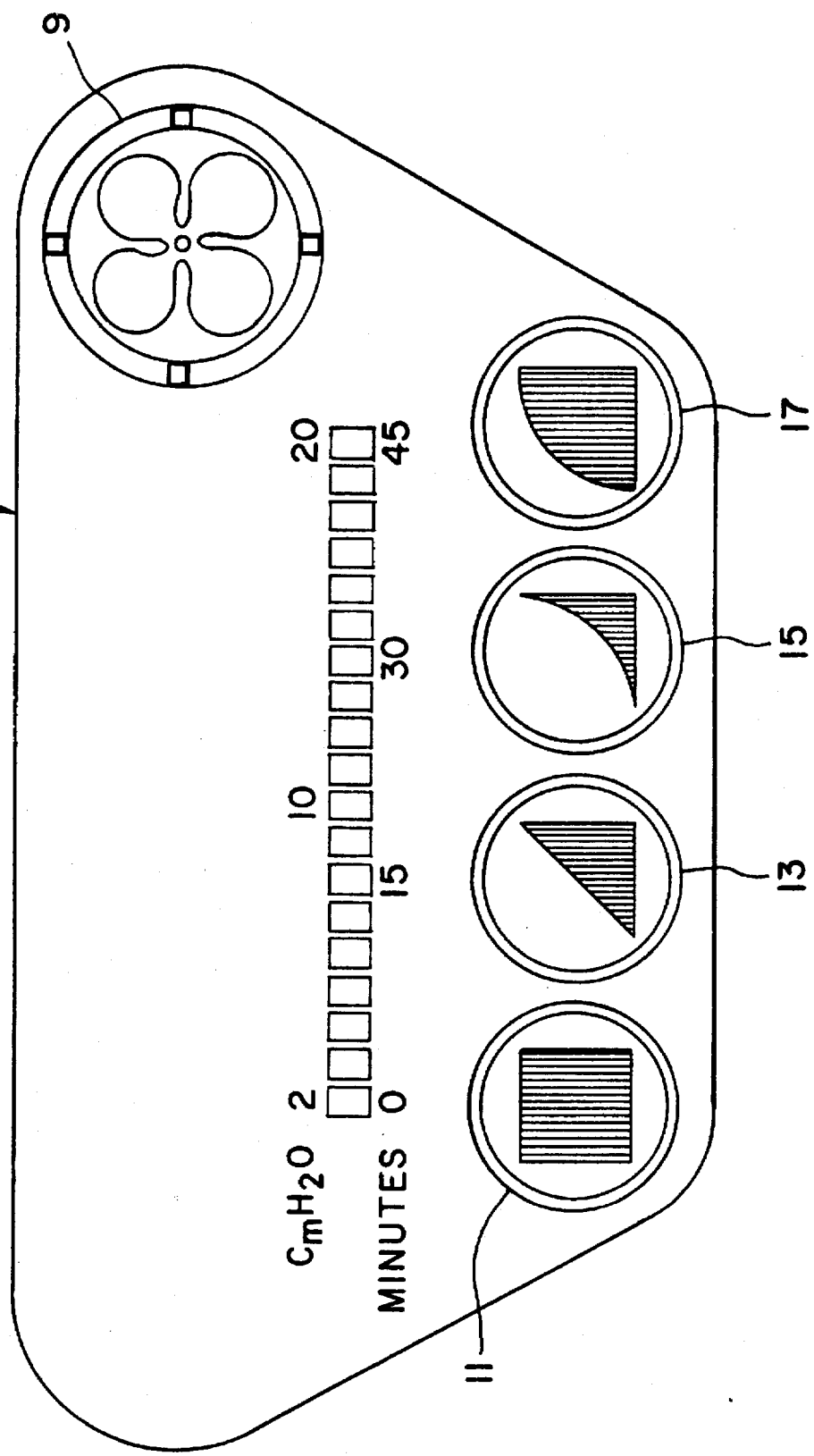
FIG. 2 is an enlarged view of the control panel of the device.
Figure 4:
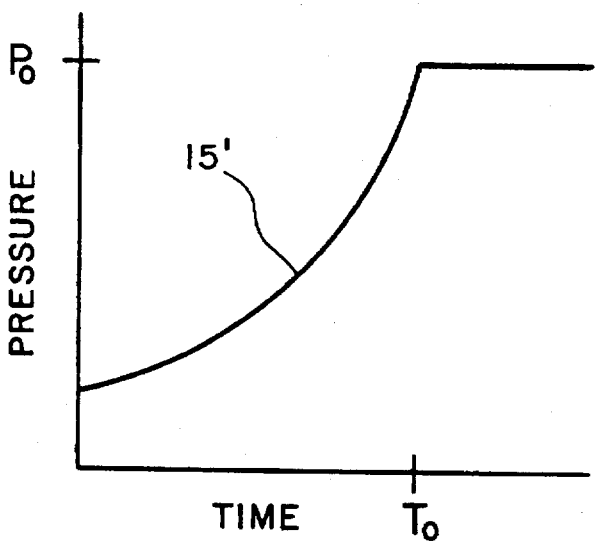
Figure 5:
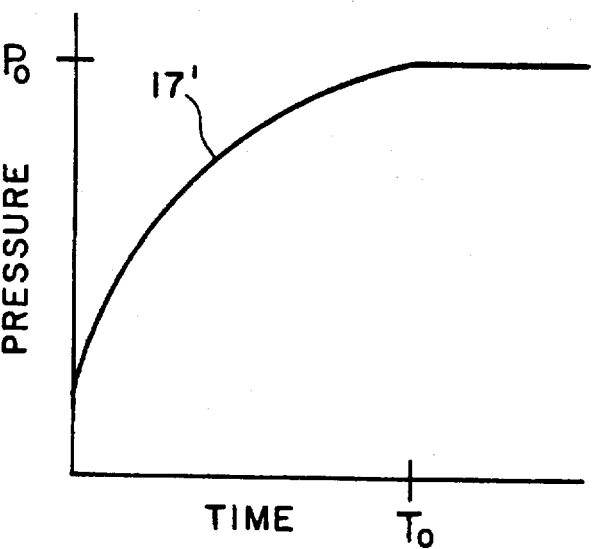

More specifically, the face 5 of the CPAP device 1 has a control panel 7 (see FIGS. 1 and 2). The panel 7 as been illustrated in FIG. 2 includes an on-off switch at 9, a non-ramp start-up actuator at 11, and a choice of three start-up ramp paths at 13, 15, and 17. In one mode of operation and with the pressure switch 9 depressed and the CPAP device 1 on, the blower or fan 3 of FIG. 1 will generate a nominal or base line pressure (e.g., two centimeters of water). Thereafter, the patient 2 desiring a ramp-up to his or her therapeutic pressure $P_o$ over his or her therapeutic ramp time interval $T_o$ can select and depress one of the three pressure switches or button actuators 13, 15, 17. If for example the patient 2 selects the ramp path graphically or pictorially represented on actuator 13 in FIG. 2, the ramp will follow the linear (e.g., 45 degree) path 13' of FIG. 3. This ramp path 13' ascends linearly from the nominal blower pressure (e.g., two centimeters of water) to the predetermined, fixed, initial therapeutic pressure $P_o$ (e.g., ten centimeters of water) over the predetermined, fixed, initial time interval $T_o$ (e.g., 30 minutes). Similarly, if the patient 2 desires an initially slower or decelerating path to the prescribed pressure $P_o$ and time $T_o$, he or she can select actuator 15 which will cause the blower 3 to follow the ramp path 15' of FIG. 4. The third ramp path 17' of FIG. 5 is then an initially faster or accelerating ramp to the prescribed pressure $P_o$ and time $T_o$.

Figure 6:
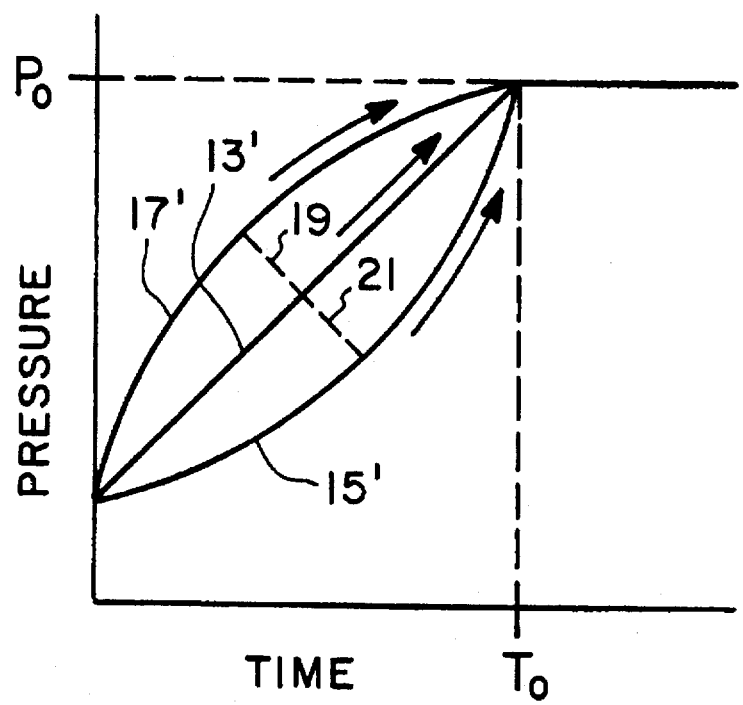
FIG. 6 illustrates the initial ramp paths superposed on each other.
Figure 7:
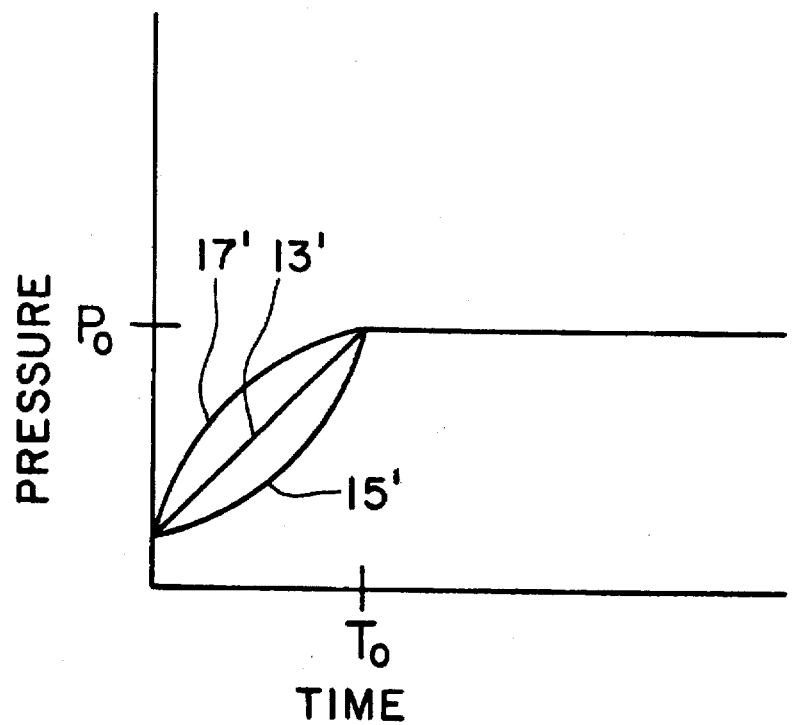
FIG. 7 illustrates how the ramp paths in the preferred embodiment maintain their same relative shapes even when the initial pressure and time settings are changed by the care giver. The sizes of the ramp paths then change but not their relative shapes.

In the preferred embodiment as shown in FIG. 6 (which illustrates the three ramp paths superposed on each other), the curved ramp paths 15' and 17' are substantially mirror images of each other about the linear ramp path 13' and respectively approach the initial time $T_o$ and initial pressure $P_o$ substantially asymptotically. Each of the curved ramps 15' and 17' in the preferred embodiments differs in pressure at 19 and 21 in FIG. 6 from the linear ramp 13' no more than about 15% to 20%. These three ramp paths 13', 15', and 17' then offer the patient 2 a fairly comprehensive choice of start-up ramps. However, like the settings for the therapeutic pressure $P_o$ and time interval $T_o$, the shapes of these ramp paths 13', 15', and 17' are fixed and predetermined and are not adjustable by the patient 2. Additionally, in the preferred embodiments, these shapes are also not adjustable even by the care giver and are pre-set by the manufacturer of the device 1 as simply a non-adjustable feature. If the care giver then changes the initial therapeutic pressure and time settings $P_o$ and $T_o$ (e.g., to respectively lesser ones as illustrated in FIG. 7), the ramp sizes change but not the shapes as the ramp paths 13', 15', and 17' simply change proportionally.

As discussed above, the settings for the initial therapeutic pressure $P_o$ and initial time interval T are non-adjustable by the patient 2. This non-adjustable feature can be accomplished in any number of manners. For example, a special tool available only to the care giver may be required for any changes or a special coded entry and exit known only to the care giver may be used. In this last regard and for example, the control panel 7 may have a special coded entry (e.g., holding down a pair or certain of the buttons 11, 13, 15, and 17 together or actuating them in a special sequence) to place the device 1 in a change mode. Once in the change mode (e.g., by depressing two of the four buttons together), operation of others of the buttons in the change mode would then selectively raise or lower the pressure and/or time setting (e.g., depress and hold one of the entry code buttons and selectively actuate second and third of the buttons for up and down). Time lapse or an exit code might also be provided. These special entry, change, and exit codes would not be made available to the patient 2. Rather, the care giver would simply set the device 1 and then provide the pre-set device 1 to the patient 2 for his or her use in the manner previously discussed.

Figure 8:
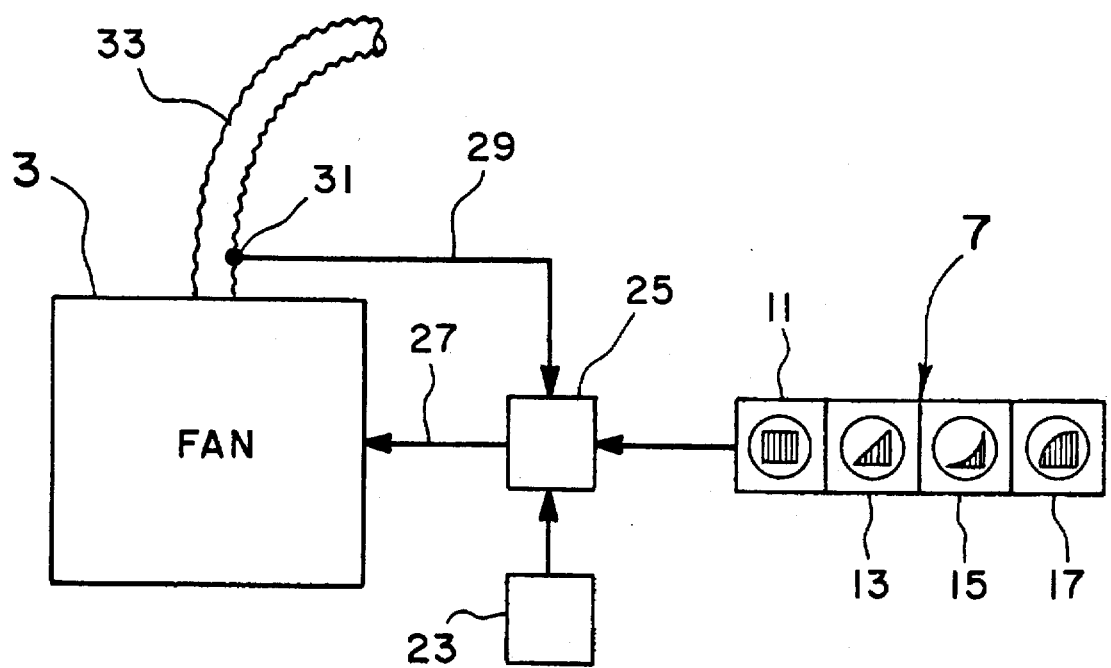
FIG. 8 is a schematic illustration of the operation of the start-up ramp system of the present invention.

Schematically as shown in FIG. 8, the care giver by his or her coded entry as schematically represented by box 23 would set or command the controller 25 to operate the variable speed blower or fan 3 to reach the prescribed therapeutic pressure $P_o$ over the prescribed time interval $T_o$. Once set, the patient 2 can then select the desired start-up ramp to get to pressure $P_o$ over time interval $T_o$ by depressing actuator 13, 15, or 17. The controller 25 via the closed-loop feedback arrangement of 27 and 29 then alters the speed of fan 3 and preferably monitors the fan's outlet pressure (e.g., by pressure transducer 31 sensing the pressure in hose 33 leading to the patient 2) to follow the path of the selected ramp shape 13', 15', or 17'. The loop also could simply monitor the fan's speed rather than pressure. This monitoring and altering of the speed and/or output pressure of the fan 3 to match the selected ramp path continues over the fixed time interval $T_o$ until the initial therapeutic pressure $P_o$ is reached. At that point, the initial therapeutic pressure $P_o$ is simply maintained if the CPAP device is a monolevel one or is selectively switched between high and low positive levels in a known manner to operate in a bilevel mode. Regardless of whether the CPAP device 1 is a monolevel or bilevel one and regardless of which ramp path 13', 15', or 17' is selected by the patient 2, the start-up ramp will reach the prescribed therapeutic pressure $P_o$ only after the prescribed time interval $T_o$ has lapsed.

While several embodiments of the present invention have been shown and described in detail, it is to be understood that various changes and modifications could be made without departing from the scope of the invention.

I claim:

1. A start-up, time-pressure ramp system including a CPAP respiratory device to offer a patient a choice of at least two, time-pressure ramp paths over a predetermined, fixed, initial time interval to a predetermined, fixed, initial therapeutic pressure, each of said fixed, initial time interval and said fixed, initial therapeutic pressure being non-adjustable by the patient and each of said ramp paths reaching said predetermined, fixed, initial therapeutic pressure only after said predetermined, fixed, initial time interval has lapsed, said CPAP respiratory device having means for delivering variable pressure levels of air over variable time intervals to the patient and means for setting said variable pressure delivering means to reach a predetermined, fixed, initial therapeutic pressure over a predetermined, fixed, initial time interval, said setting means being non-adjustable by the patient, said CPAP respiratory device further including means for selectively operating said pressure delivering means to reach said predetermined, fixed, initial therapeutic pressure over said predetermined, fixed, initial time interval by said at least two, time-pressure ramp paths, each of said ramp paths being predetermined and reaching said predetermined, fixed, initial therapeutic pressure only after said predetermined, fixed, initial time interval has lapsed, said selectively operable means for said pressure delivering means including at least first and second actuators, said first actuator causing said pressure delivering means to follow a first of said two, time-pressure ramp paths and said second actuator causing said pressure delivering means to follow a second of said two, time-pressure ramp paths, said first and second actuators being selectively operable by the patient to thereby offer the patient the choice of at least two, time-pressure ramp paths over said predetermined, fixed, initial time interval to said predetermined, fixed, initial therapeutic pressure.

2. The ramp system of claim 1 wherein each of said actuators has a graphic representation associated therewith of the ramp path caused thereby to be followed by said pressure delivering means wherein the patient can visually see which ramp path the patient wishes to selectively operate.

3. The ramp system of claim 1 wherein said first ramp path is substantially linear and said second path is substantially curved.

4. The ramp system of claim 3 further including a third ramp path.

5. The ramp system of claim 4 wherein said third ramp path is substantially curved and is substantially a mirror image of said curved, second ramp path.

6. The ramp system of claim 5 wherein said curved, third ramp path substantially asymptotically approaches said predetermined, fixed, initial therapeutic pressure.

7. The ramp system of claim 6 wherein said curved, second ramp path substantially asymptotically approaches said predetermined, fixed, initial time interval at said predetermined, fixed, initial therapeutic pressure.

8. The ramp system of claim 3 wherein said curved, second ramp path substantially asymptotically approaches said predetermined, fixed, time interval at said predetermined, fixed, initial therapeutic pressure.

9. The ramp system of claim 8 further including a third ramp path, said third ramp path being substantially a mirror image of said curved, second ramp path.

10. The ramp system of claim 3 wherein the largest difference in pressure between the linear, first ramp path and the curved, second ramp path is about 15% to 20%.

11. The ramp system of claim 1 wherein each of said ramp paths is non-adjustable by the patient.

12. The ramp system of claim 1 wherein each of said ramp paths has a shape and each of said shapes is non-adjustable by the patient.

13. The ramp system of claim 12 wherein each of said shapes is pre-set in said CPAP respiratory device and is non-adjustable.

14. A method of operating a CPAP respiratory device to offer a patient a choice of at least two, time-pressure ramp paths over a predetermined, fixed, initial time interval to a predetermined, fixed, initial therapeutic pressure, said method including the steps of:

(a) providing said CPAP respiratory device with means for delivering variable pressure levels over variable time intervals to the patient, (b) having a care giver other than the patient set the pressure delivering means to reach a predetermined, fixed, initial therapeutic pressure over a predetermined, fixed, initial time interval in a manner non-adjustable by the patient, (c) providing the CPAP respiratory device with means for selectively operating the pressure delivering means to reach said predetermined, fixed, initial therapeutic pressure over said predetermined, fixed, initial time interval by said at least two, time-pressure ramp paths wherein each of said ramp paths is predetermined and reaches said predetermined, fixed, initial therapeutic pressure only after said predetermined, fixed, initial time interval has lapsed, (d) allowing the patient to select one of said two, predetermined ramp paths, and (e) causing the pressure delivering means to follow the ramp path selected by the patient in step (d) to reach said predetermined, fixed, initial therapeutic pressure over said predetermined, fixed, initial time interval.

15. The operating method of claim 14 further including the steps of providing the CPAP respiratory device with an actuator for each ramp path and providing each actuator with a graphic representation of said ramp path activated thereby wherein the patient can visually see which ramp path the patient wishes to select.

16. The operating method of claim 14 further including the limitations of making a first of said ramp paths linear and making a second of said ramp paths curved.

17. The operating method of claim 16 further including the step of providing a third ramp path.

18. The operating method of claim 17 further including the limitations of making said third ramp path substantially a mirror image of said curved, second ramp path.

19. The operating method of claim 14 further including the step of making the ramp paths non-adjustable by the patient.

20. The operating method of claim 14 further including the step of making the shapes of the ramp paths non-adjustable by the care giver and the patient.

* * * * *